United States Patent [19]
Eisch et al.

[11] Patent Number: 5,726,332
[45] Date of Patent: Mar. 10, 1998

[54] SYNTHESIS OF NOVEL ORGANOMETALLICS AND THEIR USE IN OLEFIN POLYMERIZATION

[75] Inventors: John J. Eisch, Binghamton, N.Y.; Wolfram Uzick, Bergkamen, Germany; Katrin MacKenzie, Binghamton, N.Y.; Stefan Gurtzgen; Rainer Rieger, both of Bergkamen, Germany

[73] Assignees: Witco GmbH, Bergkamen, Germany; The Research Foundation of the State University of New York, Albany, N.Y.

[21] Appl. No.: 641,502

[22] Filed: May 1, 1996

Related U.S. Application Data

[60] Provisional application No. 60/004,119 Sep. 21, 1995.
[51] Int. Cl.$^6$ .................................. C07F 3/00; C07F 5/00; C07F 7/00
[52] U.S. Cl. .................................. 556/1; 556/95; 556/186; 556/187; 502/103; 502/117; 526/160; 526/348.2; 534/15
[58] Field of Search .................................. 556/1, 95, 186, 556/187; 526/160, 348.2; 502/103, 117; 534/15

[56] References Cited

U.S. PATENT DOCUMENTS 2,827,446   3/1958   Breslow .................................. 260/94.9

FOREIGN PATENT DOCUMENTS 1814287   8/1969   Germany.

OTHER PUBLICATIONS

FeBenbecker et al., Chem. Ber., vol. 123, pp. 2273–2278, 1990.
Breslow, David S. "BIS–(Cyclopentadienyl)–Titanium Dichloride–Alkylaluminum Complexes as Catalysts for the Polymerization of Ethylene" *Communications to the Editor*, 1957, vol. 79, pp. 5072–5073.
Natta, G. "Isotactic Polymers" *Chemistry and Industy*, 1957, pp. 1520–1530.
Natta, G. "Crystalline High Polymers of α–Olefins" *Communications to the Editor*, 1955 vol. 77 pp. 1708–1710.
Sata, Tadashi "The Reaction of Trialkylstannylmethyllithium with α, β–Epoxy Ketones and α–Chloro Ketones$^1$" *Tetrahedron*, 1991 vol. 47, pp.3281–3304.
Sinn, Von Hansjörg, "Lebende Polymere" bei Ziegler–Katalysatoren extremer Produktivitat *Verlag Chemie*, 1980 pp. 396–402.
Ziegler, K. *Angew. Chemie*, 1995 vol. 67, pp. 213.

*Primary Examiner*—Porfirio Nazario-Gonzalez
*Attorney, Agent, or Firm*—Scully, Scott, Murphy & Presser

[57] ABSTRACT

Novel bimetallic organometallic compounds, their synthesis and application in polymerization catalyst system based on combination of such novel bimetallic organometallic compounds with transition metal complexes is provided.

7 Claims, No Drawings

SYNTHESIS OF NOVEL ORGANOMETALLICS AND THEIR USE IN OLEFIN POLYMERIZATION

RELATED APPLICATIONS

This application claims the benefit of U.S. Provisional application Ser. No. 60/004,119, filed Sep. 21, 1995.

1. Field of the Invention

The present invention relates to novel organometallic compounds which have, at least, two metal centers situated on the carbon skeleton of the molecule, such that these metal centers are situated on the same carbon (geminal), on neighboring carbons (vicinal) or on carbons separated by one or more carbon atoms and yet spatially proximate, and to a method for synthesizing the same.

The present invention also provides a catalyst system for the polymerization of carbon-carbon-unsaturated compounds which comprises the aforementioned organometallic compound and a transition metal complex. A process for polymerizing unsaturated monomers, such as olefins, conjugated and unconjugated dienes, acetylenes, vinyl halides, vinylic ethers and vinylic esters, under polymerization conditions using the foregoing catalyst system of the instant invention is also provided.

2. Background of the Invention

It is well-known that certain aluminum alkyls such as ethylaluminum chlorides form heterogeneous olefin polymerization catalysts in combination with titanium tetrachloride, as is evident from K. Ziegler, Angewandte Chemie, 67, (1955) p. 213; and Natta et al., J. Am. Chem. Soc., 77 (1955) p. 1708. U.S. Pat. No. 2,827,446 to Breslow provides a modified version of those first generation catalysts wherein triethylaluminum was used as the cocatalyst instead of diethylaluminum chloride.

Typical Ziegler-Natta catalysts are all heterogeneous systems, which means that complicated surface phenomena strongly influence the catalyst performance. Many attempts have been made to explain and also to modify the performance of such so-called multiple-site catalysts.

A very early and important approach was that of G. Natta, Chem. Ind, 39, (1957) p. 1032; and Breslow et al., J. Am. Chem. Soc., 79, (1957) p. 5073, ibid 81 (1989) p. 81 in using a soluble transition metal compound/aluminum alkyl system in order to study the mechanism of Ziegler-Natta catalysis in homogeneous media.

It was found that the combination of diethylaluminum chloride and titanocene dichloride resulted in an ethylene polymerization catalyst. However, the activity of this catalyst was found to be much less than the heterogeneous Ziegler-Natta catalysts.

The next milestone of olefin polymerization catalysis was marked by H. Sinn and W. Kaminsky, who determined that partly hydrolyzed aluminum alkyls known as aluminoxanes are highly effective cocatalysts for metallocene-type transition metal complexes. In particular, the combination of metallocenes based on zirconium, titanium and hafnium with methyl aluminoxane (MAO) was found to yield much more active polymerization catalysts than the usual heterogeneous Ziegler-Natta catalysts in many olefin polymerization reactions (See, Sinn et al., Angew Chem., 92 (1980) p. 39.

Besides their very high polymerization activity, the Kaminsky-Sinn metallocene/methyl aluminoxane catalysts have additional advantageous features which include: access to new polymer modifications as to chemical, physical and mechanical properties; access to new polymer structures including specific comonomer incorporation, highly stereoselective polymerization and the reduction of undesirable side-product formation.

Because of these important advantages, metallocene-based "single-site" catalysts have unleashed a technology revolution in industrial olefin polymerization and this impact is reflected in the rapidly increasing amount of literature in this field.

Despite the numerous advantages noted above, the particular application of MAO as the cocatalyst for metallocenes introduces some intractable problems with this technology. One such problem is that a considerable excess of methylaluminoxane compared to the amount of metallocene is required in order to get a satisfactory polymerization activity. Typically the transition metal/aluminum molar ratio is between 1:100 and 1:2000. Furthermore, MAO is readily soluble only in aromatic hydrocarbons, and hence these rather unfavorable solvents must be used in any homogeneous polymerization process.

A further complication in the use of MAO arises from the limited shelf-life of methyl-aluminoxane in aromatic hydrocarbons: aging can cause gel formation in such MAO solutions and thus hinder the preparation of homogeneous catalyst systems.

Because of the importance of single-site catalysts, persistent attempts have been made to overcome the MAO-related problems by modifying MAO through incorporation of higher alkyl groups (i.e. isobutyl groups) or supporting the cocatalyst on silica or other inorganic carriers.

Even if these cocatalysts modifications eventually solve most of the above-mentioned problems, other problems may arise in their turn, namely the reduced polymerization activity of MAO modified through incorporation of higher alkyl groups and the insolubility of supported MAO, which restricts its application to slurry and gas-phase processes.

Another approach has been to find a surrogate for MAO by using ionic complexes based on perfluorophenylboron compounds (i.e. $NH_4^+[B(C_6F_5)_4]^-$) or tris (pentafluorophenyl)borane to convert the metallocene into an active, homogeneous olefin polymerization catalyst.

The main advantage of such systems is that high polymerization activity is achieved at a stoichiometric metallocene/activator ratio of 1:1. However, again certain disadvantages are encountered with these systems including that such catalyst systems are highly sensitive to impurities which are unavoidably present in large-scale productions. It should be noted that the presence of such impurities may cause severe problems in conducting the polymerization in a reliable and reproducible manner. Furthermore, some organoboron compounds exhibit considerable toxicity, which is undesirable for applications wherein the resulting polymers is used for food packaging.

In view of the disadvantages noted in the prior art polymerization catalysts, there is still need for improved, versatile, high-performance olefin polymerization catalysts.

In particular, there is still a demand for novel "single-site" catalysts which exhibit improved properties like high polymerization activity, good comonomer incorporation, high stereoselectivity of polymerization with reduced side-product formation, outstanding mechanical properties and excellent processability.

SUMMARY OF THE INVENTION

Accordingly, it has now been discovered that certain organometallic compounds form highly active olefin polymerization catalysts when combined with transition metal complexes. These novel organometallic compounds of the instant invention are characterized by containing at least two metal centers situated on the carbon skeleton of the molecule, such that the metal centers are situated on the same carbon (geminal), on neighboring carbons (vicinal) or on carbons separated by one or more carbon atoms and yet spatially proximate to each other.

Particularly, in the latter case, the three-dimensional arrangement of the atoms in the molecule makes the metal centers spatially near to each other, such that they can function as Lewis acid sites in a concerted manner. The nature of the metal centers covers a variety of types, but is preferably a main group metal from Groups 2, 13 and 14 of the Periodic Table of the Elements (this nomenclature represents the new expanded version of the Periodic Table with vertical columns or families numbered from 1 to 18 in a left to right sequence; See Van Nostrand's Scientific Encyclopedia 7th Edition, 1989 pp. 2158 and 2159).

The transition metal complexes are metallocene-type complexes which are selected from sandwich-type structures, wherein a tetravalent transition metal exhibits π-bonding to two substituted or non-substituted cyclopentadienyl, indenyl or fluorenyl ligands and σ-bonding to two other groups. The transition metal complexes can also be selected from half-sandwich-type structures, wherein a tetravalent transition metal exhibits π-bonding to one substituted or non-substituted cyclopentadienyl, indenyl or fluorenyl ligand and σ-bonding to three other groups.

Because of aforementioned structural features of the transition metal complexes and the organometallic compound, the latter component is capable of exerting a Lewis acid chelating action on the transition metal complex and thus, may generate coordinatively unsaturated, neutral or cationic transition metal centers that induce polymerization of an unsaturated organic monomer.

The unexpected polymerization activity of the catalyst system of the instant invention, with regard to unsaturated organic monomers, particularly olefins, is also covered by this invention.

The present invention also provides a method for synthesizing the aforementioned organometallic compounds by means of regioselective electrophilic substitution and metal-metal exchange reactions. It should be noted that the synthesis and work-up methods employed in the instant invention achieve the aforementioned structural features as well as the appropriate purity of the target compounds as suitable cocatalysts in Ziegler-Natta polymerizations.

DETAILED DESCRIPTION OF THE INVENTION

As stated hereinabove, the present invention relates to novel organometallic compounds which contain at least two main group metal centers from Groups 2, 13 and 14 of the Periodic Table of Elements, as well as their synthesis and their application as olefin polymerization cocatalysts when combined with certain transition metal complexes.

More specifically, the present invention describes the preferred molecular structures of the novel organometallic compounds as 1,1 and 1,2-dimetallated saturated and olefinic hydrocarbons and benzene derivatives having one of the following structural formulas (I), (II) or (III):

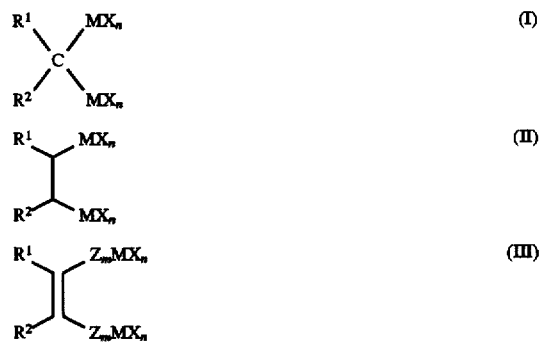

wherein M is a divalent, trivalent or tetravalent metal from Group 2, 13 or 14 of the Periodic Table of Elements, i.e. Mg, B, Sn, and preferably Al; $R^1$ and $R^2$ are independently hydrogen or one to four long-chained, branched or cyclic alkyl groups with or without further substitution, or a cyclic skeleton such that $R_1$ and $R_2$ form an optionally saturated, unsaturated, substituted or unsubstituted cyclic structure; X is a halogen (Cl, Br, F) or a substituted or unsubstituted methyl, alkyl or a substituted or unsubstituted phenyl or benzyl group; n is 1 for divalent, 2 for trivalent and 3 for tetravalent metals; Z is a methylene group (—$CH_2$—); and m is 0, 1 or 2.

Typical examples of organometallic compounds which satisfy the above structural formulas include, but are not limited to:

type (I): bis(chloro(methyl))alumino)methane type (II): 1,2-bis(chloro(methyl)alumino)ethane type (III): cis-1,2-bis(chloro(methyl)alumino)ethene, 1,2-bis(chloro(methyl)alumino)benzene These examples are intended to illustrate the Lewis acidic and chelating character of the organometallic compounds of the instant invention.

Since these compounds have not been previously described in the prior art, the instant invention also provides a process for synthesizing such compounds.

Typically in the present invention, a dihalogenated hydrocarbon is allowed to react i.e. with magnesium metal in an ether solvent in order to prepare a di-Grignard reagent. A reaction analogous to such a Grignard reaction, in an ether or hydrocarbon solvent with lithium metal or with an alkyllithium reagent, is also contemplated herein.

The organometallic intermediate thus provided is then transformed into the target molecule either directly or via its boron, tin or silicon derivative by means of metal-metal substitution and careful work-up procedures. Detailed methods for such preparation are illustrated in the examples of the instant invention.

Reaction Scheme (e.g.)

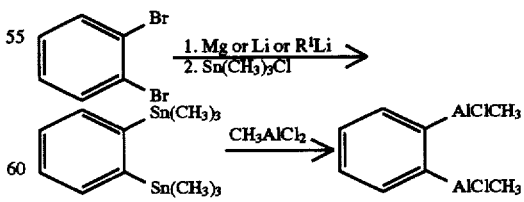

As described above, the novel organometallic compounds are capable of activating specific transition metal complexes in such a way that polymerization of unsaturated compounds is induced very effectively. From the prior art it is known that metallocene-type transition metal complexes form active species for olefin polymerization when allowed to react i.e. with aluminum alkyls or boron compounds. These previous studies also offer evidence for certain mechanistic details, such as ion pair formation, catalyst deactivation and the role of MAO or pentafluorinated phenylboron compounds as state-of-the-art cocatalysts.

However, no prior art is known which deals with the employment of bimetallic molecules as cocatalysts for metallocenes or related transition metal compounds. Therefore, the instant invention also provides for the formation of highly active polymerization catalysts which comprise the combination of the aforementioned organometallic compounds and a transition metal complexes, particularly with sandwich-type transition metal complexes, where a tetravalent transition metal exhibits $\pi$-bonding to two substituted or non-substituted cyclopentadienyl, indenyl or fluorenyl ligands and $\sigma$-bonding to two other substituents. The transition metal complexes may also be selected from half-sandwich-type structures, where a tetravalent transition metal exhibits $\pi$-bonding to one substituted or non-substituted cyclopentadienyl, indenyl or fluorenyl ligands and $\sigma$-bonding to three other substituents. Such compounds are well known to those skilled in the art and have become known as metallocenes.

The structural formula of transition metal compounds that may be employed in the instant invention is illustrated by the following formula:

$$Q_m(CpR_a)(Cp'R'_{a'})M(CH_3)_nX_{2-n}$$

wherein Cp is a cyclopentadienyl, indenyl or fluorenyl group; R and R' are the same or different and are hydrogen, substituted or unsubstituted alkyl or aryl groups containing from 1 to 12, preferably 1 to 8, carbon atoms; a and a' are the same or different and are numbers between 0 and 5; Cp' is a Cp ligand or nitrogen, with the proviso that when Cp' is nitrogen, R' is an alkyl or aryl group, a'=1 and m=1; Q is a bridging group $(R^1—Y—R^2)_b$ between Cp and Cp' where $R^1$ and $R^2$ represent either hydrogen or a $C_1$–$C_{10}$ alkyl group or a $C_6$–$C_{10}$ aryl group; Y is carbon, germanium or silicon; b is a number between 1 and 3, M is a transition metal from Groups 4, 5 or 6 of the Periodic Table of Elements, preferably hafnium, titanium or zirconium; X is a halogen; n is a number between 0 and 2; and m is 0 or 1.

Synthesis of these metallocenes can be performed according to existing literature descriptions.

As indicated hereinabove the present invention also relates to the use of the catalyst system of the instant invention for the polymerization of unsaturated compounds. Preferred compounds for polymerization are olefins, but other unsaturated monomers exemplified by, but not limited to, acetylenes, conjugated and non-conjugated dienes, vinylic halides, ethers and esters are also contemplated herein.

Table 1 illustrates the outstanding polymerization performance of the catalyst system of the instant invention.

TABLE 1

Polymerization performance exhibited by the bimetallic organometallic compounds of the instant invention as cocatalysts compared with known aluminum alkyls when combined with transition metal complexes. For explanation of procedures 1, 2, 3, please refer to the Examples.

| Novel bimetallic compound | molar Ratio Ti:Al | Solvent | Productivity numbers [g/(gTi·h·bar)] procedure 1 | 2 | 3 |
|---|---|---|---|---|---|
|  AlClCH$_3$ / AlClCH$_3$ | 1:8  1:16 | PhMe PhMe | 2 340 3 000 | 2 828 | 1 951 |
| CH$_2$AlClCH$_3$ / AlClCH$_3$ | 1:8 | PhMe | 1 925 | | |
| MAO | 1:8 | PhMe | 810 | 610 | 1 295 |
| MeAlCl$_2$ | 1:8 | C$_6$H$_{14}$ | 195 | 316 | |
| Et$_2$AlCl | 1:8 | PhMe | | | 227 |

As can be seen from these data, the novel organometallic compounds according to this invention provide superior polymerization productivity when compared with known aluminum alkyls and, particularly, when compared with MAO at comparable Ti:Al ratios. Furthermore, by employing the organometallic compounds of the instant invention, as catalysts, it is not necessary to use an excess amount of the cocatalyst as is required for optimum performance when MAO is employed.

The following examples are given to illustrate the scope of this invention. Because these examples are given for illustrative purposes only, the invention embodied therein should not be limited thereto.

EXAMPLES 1–15 AND COMPARATIVE EXAMPLES 16 AND 17

The following examples of experiments include the synthesis of novel organometallic compounds and their application in polymerization when combined with various transition metal complexes.

Three different polymerization procedures were employed in the instant invention, which are described in the following procedures.

Procedure 1:

1 mmol of dicyclopentadienyl-titan-chloromethyl (methyltitanocene chloride) was used in a total volume of 100 mL of anhydrous solvent. A glass reactor containing a magnetic stirring was employed. The reaction was started at room temperature and conducted without cooling. An ethylene pressure of 2.76 bars (40.03 psi) was maintained during polymerization. The polymerization was allowed to proceed for 30 minutes unless the amount of precipitated polymer required the polymerization to be terminated sooner. The reaction was terminated by addition of methanol, the suspension of the polymer was filtered off and washed with additional amounts of ethanol and 6N aqueous HCl. The resulting polymer was dried to constant weight.

Procedure 2 and 3:

A 0.225-mmol sample of methyltitanocene chloride (procedure 2) or dicyclopentadienyl-titan-dichloride (titanocene dichloride) (procedure 3) was used in a total volume of 900 mL anhydrous solvent. A stainless steel reactor containing a mechanic stirring was employed. The reaction was conducted at a constant temperature of 30° C. An ethylene pressure of 4.0 bars (58 psi) was maintained during polymerization. The polymerization was allowed to proceed for 20 minutes unless the amount of precipitated polymer required the polymerization to be terminated sooner. The reaction was terminated by the interruption of ethylene feed and the release of ethylene pressure. The polymer yield was washed with additional amounts of toluene and dried to constant weight.

EXAMPLE 1

Preparation of bis(trimethylstannyl)methane (Type I):

The substance was synthesized by a modified literature procedure of T. Sato et al., Tetrahedron 47 (1991) 3281.

31.35 g (100 mmol) tin dibromide, 15.1 g (56.2 mmol) diiodomethane and 4 drops triethylamine (as a catalyst) were allowed to react with stirring for 17 hours at 140° C. After cooling the brown reaction mixture to 0° C., 104 ml (312 mmol) of a 3M solution of methylmagnesium bromide in diethyl ether were slowly added. After completing the addition, the solution was refluxed for 1 hour, allowed to cool to room temperature and then hydrolyzed with ice. The water layer was extracted several times with a diethyl ether/hexane mixture. After drying the combined organic layers with sodium sulfate, the solvent was removed. A vacuum distillation of the pale yellow residue (16 Torr) resulted 8.9 g of a colorless liquid (b.p. 80° C.). Yield 50%.

$^1$H-NMR (360.1 MHZ, $C_6D_6$, 25° C., δ in ppm): −0.22 s ($CH_2$) 0.08 s ($SnCH_3$, $^2J_{Sn-H}$=50.7/53.0 HZ)

$^{13}$C-NMR (90.6 MHZ, $C_6D_6$, 25° C., δ in ppm): 10.0 ($SnCH_3$, $^1J_{Sn-C}$=314.9/328.0 HZ), 17.2 ($CH_2$, $^1J_{Sn-C}$=259.8/270.3 Hz)

EXAMPLE 2

Reaction of bis(trimethylstannyl)methane, $((CH_3)_3Sn)_2CH_2$ with methylaluminum dichloride $CH_3AlCl_2$ to form bis(chloro(methyl)alumino)methane (Type I):

To 3.72 g (10.9 mmol) bis(trimethylstannyl)methane were slowly added 21.8 ml of a 1.0M solution of methylaluminum dichloride (21.8 mmol) in hexane at a temperature of −10° C. After completing the addition, the reaction mixture was allowed to warm to room temperature resulting in the formation of two layers. The phases were separated and the lower layer (a yellow oil) was treated in vacuum for several hours in order to remove all trimethyltin chloride.

$^1$H-NMR (360 MHZ, toluene, 25° C., δ in ppm): −0.38 br (1H), 0.63 s (1H), 0.85 br (6H)

EXAMPLE 3

Preparation of 1,2-bis-(trimethyltin)ethane $((CH_3)_3Sn)_2 C_2H_4$ (Type II):

8.0 g (28.7 mmol) tin dibromide, 1.4 ml (16 mmol) 1,2-dibromoethane and 4 drops triethylamine (as a catalyst) were allowed to react with stirring for 18 hours at 130° C. After cooling the reaction mixture to 0° C., 32 ml (96 mmol) of a 3M solution of methylmagnesiumbromide in diethyl ether were slowly added. After completing the addition, the solution was refluxed for 1 hour, allowed to cool to room temperature and then hydrolyzed with ice. The water layer was extracted several times with diethyl ether/hexane-mixture. After drying the combined organic layers with sodium sulfate, the solvent was removed. A vacuum distillation of the residue (10 Torr) resulted in 0.3 g of the product. (b.p.=78° C.). Yield: 7%

EXAMPLE 4

Reaction of 1,2-bis(trimethylstannyl)ethane $((CH_3)_3Sn)_2 C_2H_4$ with methylaluminum dichloride $CH_3AlCl_2$ to form 1,2-bis(chloro(methyl)alumino)ethane (Type II):

To 0.3 g (0.84 mmol) bis(trimethylstannyl)ethane were slowly added 1.7 ml of a 1.0M solution of methylaluminum dichloride (1.7 mmol) in hexane at a temperature of −10° C. After completing the addition, the reaction mixture was allowed to warm to room temperature resulting in the formation of two layers. The phases were separated and the lower layer (a yellow oil) was treated in vacuum in order to remove all trimethyltin chloride.

EXAMPLE 5

Preparation of 1,2 bis(trimethylstannyl)benzene, 1,2-$C_6H_4$ $(Sn(CH_3)_3)_2$ (Type III):

To a suspension of 3.4 g (141 mmol) magnesium in 30 ml THF was added a mixture of 50 ml (50 mmol) of a 1.0M solution of trimethyltin chloride in THF 3.0 mL (25 mmol) 1,2-dibromobenzene under sonication. The resulting reaction mixture was stirred for 3 days, then the solvent was evaporated in vacuum and the residue was extracted with 100 ml pentane. The pentane solution was filtered and the solvent was removed. A vacuum distillation of the residue (0.15 Torr) resulted in 6.0 g (14.9 mmol) of a colorless oil (b.p=80°–95° C.) Yield: 59%

$^1$H-NMR (360.1 MHZ, $C_6D_6$, 25° C., δ in ppm): 0.28 s ($SnCH_3$), 7.12 m–7.21 m ($C_6H_4$), 7.49–7.54 m ($C_6H_4$)

$^{13}$C-NMR (90.6 MHZ, $C_6D_6$, 25° C., δ in ppm): −7.0 ($SnCH_3$), 128.3 ($C_6H_4$), 137.3 ($C_6H_4$), 151.6 ($C_6H_4$)

EXAMPLE 6

Reaction of 1,2 bis(trimethylstannyl)benzene, $C_6H_4$ $(Sn(CH_3)_3)_2$ with methylaluminum dichloride $CH_3AlCl_2$ to form 1,2-bis(chloro(methyl)alumino)benzene (Type III):

To a solution of 570 mg (1.4 mmol) 1,2-bis(trimethylstannyl)benzene in 4 ml toluene were added 2.8 ml of a 1.0M solution of methylaluminum dichloride in hexane (2.8 mmol) at room temperature. After stirring for 3 days, the solvents were evaporated in vacuum. In order to remove all volatile materials, the residue was heated in vacuum up to 50° C. The residue obtained (a pale yellow wax) was analyzed by NMR.

$^1$H-NMR (360.1 MHZ, $C_6D_6$, 25° C., δ in ppm): 0.25 br ($AlCH_3$≈1.7H), 0.8 br ($AlCH_3$≈3 8H) 6.8–7.3 m, br ($C_6H_4$≈3.1H), 7.4–7.9 m, br ($C_6H_4$, 2.0H)

$^{13}$C-NMR (90.6 MHZ, $C_6D_6$, 25° C., δ in ppm): −6.6 ($AlCH_3$), 4.3 br ($AlCH_3$) 129.5 br ($C_6H_4$), 137.0 ($C_6H_4$), 150.4 ($C_6H_4$)

$^{27}$Al-NMR (78.2 MHZ, $C_6D_6$, 25° C., δ in ppm): 101 ($W_{1/2}$=5000 Hz)

EXAMPLE 7

Preparation of α,2-bis(trimethylstannyl)toluene, o-$(CH_3)_3 SnC_6H_4CH_2Sn(CH_3)_3$:

To a suspension of 5.0 g (208 mmol) magnesium in 100 ml THF was added a mixture of 18.1 g (91 mmol) trimethyltin chloride and 11.35 g (45.5 mmol) o-bromobenzyl bromide in 100 ml THF during 3 hours. After completing the addition, the resulting brown reaction mixture was refluxed for 1 hour, allowed to cool to room temperature and then hydrolyzed with ice. The water layer was extracted several times with a diethyl ether/hexane-mixture. After drying the combined organic layers with sodium sulfate, the solvent was removed. A vacuum distillation of the residue (0.15 Torr) resulted in 4.7 g of a colorless liquid (b.p.=110°–117° C.) Yield: 25%

$^1$H-NMR (360.1 MHZ, $C_6D_6$, 25° C., δ in ppm): 0.05 s (Sn $CH_3$), 0.30 s (Sn$CH_3$), 2.40 s ($CH_2$), 6.9–7.4 m ($C_6H_4$)

$^{13}$C-NMR (90.6 MHZ, $C_6D_6$, 25° C., δ in ppm): −9.5 (Sn$CH_3$), −8.1 (Sn$CH_3$), 24.2 ($CH_2$), 123.6 ($C_6H_4$), 126.8 ($C_6H_4$), 129.2 ($C_6H_4$), 136.7 ($C_6H_4$), 138.7 ($C_6H_4$), 149.8 ($C_6H_4$)

EXAMPLE 8

Reaction of α,-2-bis(trimethylstannyl)toluene, o-($CH_3$)$_3$Sn$C_6H_4CH_2$Sn($CH_3$)$_3$ with methylaluminum dichloride $CH_3AlCl_2$ to form α,-2-bis(chloro(methyl)alumino)toluene (Type III):

To 22.5 ml of a 1.0M solution of methylaluminum dichloride (22.5 mmol) in hexane were slowly added 4.7 g (11.26 mmol) α,-2-bis(trimethylstannyl)toluene at a temperature of −5° C. After completing the addition the yellow reaction mixture was allowed to warm to room temperature resulting in the formation of two layers. The lower layer (a brown oil) consisted mainly of unreacted starting material. Separation of the upper layer and evaporation of the solvent left a brown oil. In order to remove trimethyltin chloride this oil was treated in vacuum for two hours. Yield: 1.8 g (65%)

$^1$H-NMR (360.1 MHZ, toluene, 25° C., δ in ppm): −0.35 br (Al$CH_3$), 6.5–7.25 ($C_6H_4$)

EXAMPLE 9

Preparation of 1,2-dilithiobenzene, o-$C_6H_4Li_2$ (Type III):

To a solution of 6.0 g (14.9 mmol) 1,2-bis(trimethylstannyl)benzene in 20 ml pentane was added 18.6 ml (29.8 mmol) of a 1.6M solution of n-butyllithium in hexane at a temperature of −78° C. The reaction mixture was warmed to room temperature and stirred for 2 days. A white precipitate was formed during this period and was isolated by filtration, washed with 10 ml pentane and dried in vacuum. In this way 1.27 g (14.1 mmol) of the product was obtained.

EXAMPLE 10

Preparation of 1,2-bis(dimethylalumino)benzene, o-$C_6H_4$(Al($CH_3$)$_2$)$_2$ (Type III):

To a suspension of 1.68 g (18.7 mmol) 1,2-dilithiobenzene in 20 ml toluene was added via a syringe 3.5 ml (37.5 mmol) neat dimethylaluminum chloride at room temperature. After stirring the resulting yellow reaction mixture for 3 days, the precipitate formed was filtered and then yellow oil was identified as the desired product by NMR-spectroscopy. In this was 1.57 g (8.3 mmol, 44%) of the product was obtained.

$^1$H-NMR (360.1 MHZ, $C_6D_6$, 25° C., δ in ppm): −0.41 br (Al$CH_3$), −0.32 br (Al$CH_3$) 6.96 dd ($C_6H_4$), 7.96 dd ($C_6H_4$)

$^{13}$C-NMR (90.6 MHZ, $C_6D_6$, 25° C., δ in ppm): −7.7 (Al$CH_3$), −6.4 br (Al$CH_3$) 129.7 ($C_6H_4$), 144.9 ($C_6H_4$), 160.3 ($C_6H_4$)

$^{27}$Al-NMR (78.2 MHZ, $C_6D_6$, 25° C., δ in ppm): 15° C.: 174 ($W_{1/2}$=3200 Hz), −8° C.: 179 ($W_{1/2}$=5200 Hz)

Polymerization Examples Employing The Novel and Conventional Aluminum Cocatalysts with Methyltitanocene Chloride

EXAMPLE 11

In accordance with Procedure 1, 4.0 mmol of 1,2-bis(chloro(methyl)alumino)benzene were employed (Ti:Al=1:8) and the polymerization was allowed to proceed for 20 min, whereupon the precipitated polymer could no longer be stirred. The yield of polyethylene (PE) produced was 10.14 g (mp 130°–134° C.), for a productivity of 2.34 kg PE/g Ti·h·bar.

EXAMPLE 12

In accordance with Procedure 1, 4.0 mmol of 1,2-bis(chloro(methyl)alumino)benzene were employed (Ti:Al=1:16) and the polymerization was allowed to proceed for 15 min, whereupon the precipitated polymer could no longer be stirred. The yield of the polyethylene was 9.75 g (mp 130°–134° C.), for a productivity of 3.00 kg PE/g Ti·h·bar.

EXAMPLE 13

In accordance with Procedure 1, 4.0 mmol of α,2-bis(chloro(methyl)alumino)toluene were employed (Ti:Al=1:8) and the polymerization was allowed to proceed for 30 min. The yield of polyethylene was 12.53 g (mp 130°–135° C.) for a productivity of 1.93 kg PE/g Ti·h·bar.

EXAMPLE 14

In accordance with Procedure 1, 4.0 mmol of 1,2-bis(chloro(methyl)alumino)ethane were employed (Ti:Al=1:8) and the polymerization was allowed to proceed for 30 min. Yield of polyethylene was 3.58 g (mp 130°–135° C.) for a productivity of 0.55 kg PE/g Ti·h·bar.

EXAMPLE 15

In accordance with Procedure 1, 4.0 mmol of bis(chloro(methyl)alumino)methane were employed (Ti:Al=1:8) and the polymerization was allowed to proceed for 30 min. Yield of polyethylene was 1.63 g (mp 130°–133° C.) for a productivity of 0.25 kg PE/g Ti·h·bar.

Comparative Example 16

In accordance with Procedure 1, 8.0 mmol of MAO in toluene (containing 13.2% Al by weight at a concentration of 30% by weight) was employed and the polymerization was allowed to proceed for 30 min. The yield of polyethylene was 5.29 g (mp 129°–142° C.) for a productivity of 0.81 g/kg PE/g Ti·h·bar.

Comparative Example 17

In accordance with Procedure 1, 8.0 mmol of methylaluminum dichloride were employed and the polymerization was allowed to proceed for 30 min. The yield of polyethylene was 1.10 g (mp 130°–133° C.) for a productivity of 0.17 kg PE/g Ti·h·bar.

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

We claim:

1. A method for synthesizing an organometallic compound having one of the following structural formulas:

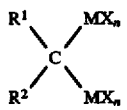 (I)

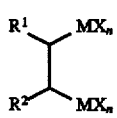 (II)

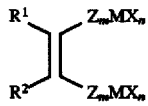 (III)

wherein M is a divalent, trivalent or tetravalent metal from Groups 2, 13 or 14 of the Periodic Table of Elements; $R^1$ and $R^2$ are independently hydrogen or long-chained, branched or cyclic alkyl groups with or without further substitution, or a cyclic skeleton such that $R_1$ and $R_2$ form an optionally saturated, unsaturated, substituted or unsubstituted cyclic structure; X is halogen or a substituted or unsubstituted methyl, alkyl or a substituted or unsubstituted phenyl or benzyl group; n is 1 for divalent, 2 for trivalent and 3 for tetravalent metals; Z is a methylene group (—$CH_2$—); and m is independently 0, 1 or 2; said method comprising the steps of:

(a) reacting a saturated, unsaturated or aromatic hydrocarbon compound containing at least two halogen substituents attached to the same (geminal) or neighboring (vicinal) carbon atoms or attached to carbon atoms separated by one or more carbons with magnesium in an ether-type solvent or reacting said halogenated hydrocarbon with lithium metal or a lithium alkyl compound in an ether-type or hydrocarbon solvent, to provide a magnesium or lithium intermediate whereby said intermediate is transformed in-situ into a boron, tin or silicon derivative through metal-metal exchange reactions by means of appropriate boron, tin or silicon reactants;

(b) transforming said boron, tin or silicon derivative into said organometallic compound by appropriate substitution reaction; and (c) isolating said organometallic compound by means of fractional distillation or recrystallization.

2. The method of claim 1 wherein the organometallic compound has the structural formula:

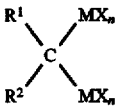

wherein M, $R^1$, $R^2$, X and n are as defined in claim 1.

3. The method of claim 1 wherein the organometallic compound has the structural formula:

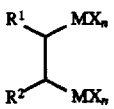

wherein M, $R^1$, $R^2$, X and n are as defined in claim 1.

4. The method of claim 1 wherein the organometallic compound has the structural formula:

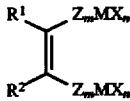

wherein M, $R^1$, $R^2$, X, Z, m and n are as defined in claim 1.

5. The method of claim 1 wherein M is Al, Mg, B or Sn.

6. The method of claim 5 wherein M is Al.

7. The method of claim 1 wherein said organometallic compound is 1,2-bis(chloro(methyl)alumino)benzene, 2,2-bis(chloro(methyl)alumino)toluene, 1,2-bis(chloro(methyl)alumino)ethane or bis(chloro(methyl)alumino)methane.

* * * * *

UNITED STATES PATENT AND TRADEMARK OFFICE
CERTIFICATE OF CORRECTION

PATENT NO. : 5,726,332
DATED : March 10, 1998
INVENTOR(S) : John J. Eisch, et al.

It is certified that error appears in the above-identified patent and that said Letters Patent is hereby corrected as shown below:

Column 1, line 27: delete "Invention" and insert --Prior Art--

Column 6, line 10: before "Productivity" insert --PE--

Column 7, lines 33 & 35: "HZ" should read --Hz--

Signed and Sealed this

Twenty-fourth Day of November, 1998

Attest:

BRUCE LEHMAN

*Attesting Officer*     *Commissioner of Patents and Trademarks*